United States Patent
Angster et al.

(10) Patent No.: US 8,302,461 B2
(45) Date of Patent: Nov. 6, 2012

(54) GAS DETECTOR HAVING AN ACOUSTIC MEASURING CELL AND SELECTIVELY ADSORBING SURFACE

(75) Inventors: Judit Angster, Stuttgart (DE); Andreas Schmohl, Munich (DE); Andras Miklos, Stuttgart (DE)

(73) Assignee: Fraunhofer-Gesellschaft zur Foerderung der Angewandten Forschung e.V., Munich (DE)

( * ) Notice: Subject to any disclaimer, the term of this patent is extended or adjusted under 35 U.S.C. 154(b) by 718 days.

(21) Appl. No.: 12/300,952

(22) PCT Filed: May 12, 2007

(86) PCT No.: PCT/EP2007/004223
§ 371 (c)(1),
(2), (4) Date: Dec. 16, 2008

(87) PCT Pub. No.: WO2007/131739
PCT Pub. Date: Nov. 22, 2007

(65) Prior Publication Data
US 2009/0183552 A1    Jul. 23, 2009

(30) Foreign Application Priority Data
May 17, 2006    (DE) .......................... 10 2006 023 061

(51) Int. Cl.
G01N 7/02 (2006.01)
(52) U.S. Cl. ..................................... 73/31.04; 73/31.05
(58) Field of Classification Search ................... 73/23.2, 73/31.04, 31.05; 250/282, 288; 356/436, 356/437
See application file for complete search history.

(56) References Cited

U.S. PATENT DOCUMENTS

| | | | |
|---|---|---|---|
| 4,067,653 A * | 1/1978 | Fletcher et al. | 356/433 |
| 5,933,245 A * | 8/1999 | Wood et al. | 356/437 |
| 6,639,217 B1 * | 10/2003 | Li | 250/288 |
| 6,707,039 B1 * | 3/2004 | Truche et al. | 250/288 |
| 6,812,455 B2 * | 11/2004 | Hillenkamp et al. | 250/288 |
| 7,034,943 B1 | 4/2006 | Moeckli et al. | |
| 7,411,183 B2 * | 8/2008 | Overney et al. | 250/282 |
| 7,462,823 B2 * | 12/2008 | Schneider | 250/288 |
| 7,578,973 B2 * | 8/2009 | Call et al. | 422/83 |

(Continued)

FOREIGN PATENT DOCUMENTS

| | | |
|---|---|---|
| DE | 199 13 220 | 7/2001 |
| FR | 2 815 122 | 4/2002 |
| JP | 6-165933 | 6/1994 |
| WO | 03/026774 | 4/2003 |

OTHER PUBLICATIONS

Beck et al., "Surface Screening of Pentachlorophenol by Thermodesorption Sampling and Photoacoustic Detection", Analytical Sciences, vol. 17, Apr. 2001.*

(Continued)

Primary Examiner — David Rogers
(74) Attorney, Agent, or Firm — Greenblum & Bernstein, P.L.C.

(57) ABSTRACT

A gas detector with a selectively adsorbing surface (3) and an acoustic measuring cell (5) is presented. The detector is characterized in that the selectively adsorbing surface (3) and the acoustic measuring cell (5) can be arranged with respect to one another such that gases desorbed by means of thermal desorption from the adsorbing surface (3) reach the acoustic measuring cell (5) and there trigger a pressure wave that can be measured by one or more acoustic pick-ups (13, 14), in particular microphones, which are arranged in the acoustic measuring cell (5). Furthermore, a corresponding method is provided. The detector is particularly suitable for measuring contaminants in interior spaces and ventilation systems.

23 Claims, 2 Drawing Sheets

U.S. PATENT DOCUMENTS

| | | | |
|---|---|---|---|
| 7,619,217 B2* | 11/2009 | Shea et al. | 250/288 |
| 7,765,871 B2* | 8/2010 | Riddle | 73/590 |
| 7,808,640 B2* | 10/2010 | Fritz et al. | 356/432 |
| 2002/0007687 A1 | 1/2002 | Zimmerman et al. | |
| 2002/0109085 A1* | 8/2002 | Hillenkamp et al. | 250/288 |
| 2003/0052268 A1* | 3/2003 | Doroshenko et al. | 250/288 |
| 2004/0183009 A1* | 9/2004 | Reilly et al. | 250/288 |
| 2005/0194544 A1* | 9/2005 | Vestal et al. | 250/425 |
| 2006/0192966 A1 | 8/2006 | Moeckli et al. | |
| 2006/0255289 A1* | 11/2006 | Cygan et al. | 250/442.11 |
| 2007/0131871 A1* | 6/2007 | Chang et al. | 250/427 |
| 2008/0308722 A1* | 12/2008 | Shiea | 250/281 |
| 2010/0027012 A1* | 2/2010 | Fritz et al. | 356/432 |

OTHER PUBLICATIONS

Theodore Heise, "Investigations into Ultraviolet Matrix-Assisted Laser Desorption", Jan. 20, 1994.*

Rosengren, "Optimal optoacoustic detector design", Applied Optics, vol. 14, No. 8, Aug. 1975, pp. 1960-1976.

Miklós et al., "Multipass acoustically open photoacoustic detector for trace gas measurements", Applied Optics, vol. 45, No. 11, Apr. 10, 2006, pp. 2529-2534.

* cited by examiner

GAS DETECTOR HAVING AN ACOUSTIC MEASURING CELL AND SELECTIVELY ADSORBING SURFACE

CROSS-REFERENCE TO RELATED APPLICATIONS

The present application is a U.S. National Stage of International Patent Application No. PCT/EP2007/004223 filed May 12, 2007, and claims priority of German Patent Application No. 10 2006 023 061.2-52 filed May 17, 2006. Moreover, the disclosure of International Patent Application No. PCT/EP2007/004223 is expressly incorporated by reference herein in its entirety.

BACKGROUND OF THE INVENTION

The present invention relates to a gas detector with an acoustic measuring cell and a selectively adsorbing surface.

Essentially, four possibilities are available for detecting gases: In the measurement with sampling, constituents of the gas phase are collected on an adsorber. For analysis, the adsorbed constituents are transferred into the gas phase again. This method permits enrichment of the constituents of interest. The collection on adsorber tubes with subsequent thermal desorption (TD), use gas chromatography (GC) for fractionation and a mass-selective detector (MSD) or flame ionization detector (FID) for detection, which are cited by way of example. The advantages are the selectivity and the low detection limit. However, real-time measurements cannot be carried out with chromatographic methods.

With direct measurement in the gas phase (e.g., fluorescence, IR spectroscopy, UV/VIS spectroscopy, photoacoustics), enrichment as well as pre-separation of the constituents are omitted. These disadvantages—in particular with reference to selectivity—can be expensive to overcome.

Another possibility for detecting gases is through measurement with chemical conversion of the analyte. The conversion can be carried out on a surface or in a solution. Two methods can be distinguished:
a) Those in which a reactant has to be fed to the system. These systems are maintenance-intensive due to the consumption of chemicals and thus not economically justifiable for many applications.
b) Those in which the reactant is atmospheric oxygen. The differentiation of the constituents of interest from the matrix is carried out by a more or less selective reaction, i.e., the selective oxidation at certain heated metal oxide surfaces. Here, low selectivity can also be expensive to overcome.

Furthermore, a measurement by changing physical properties on or at a surface is known. For example, quartz balances and surface-wave detectors are used for this purpose. Physical detectors, however, are problematic because of their low selectivity.

DE 199 13 220 C2 describes a collecting medium that has a selectively adsorbing surface. Substances to be examined can be adsorbed on such a surface. The substances can then be desorbed again for a subsequent measurement. This desorption can also be carried out thermally. DE 199 13 220 C2, for example, mentions, inter alia, photoacoustics as a possible measurement method for determining which substance has been desorbed. Consequently, DE 199 13 220 C2 discloses a measuring device in which the gases desorbed from an adsorbing surface can be examined photoacoustically. The desorbed gases are excited by a light source, normally a laser, in order to generate a photoacoustic signal through absorption. WO 03/026774 A1 also discloses a device, which can photoacoustically examine gases desorbed from a surface.

SUMMARY OF THE INVENTION

The present invention provides a gas detector and a method for analyzing gas constituents which renders possible high selectivity and quick measurements with low equipment costs.

According to the invention, the gas detector has a selectively adsorbing surface and an acoustic measuring cell. The selectively adsorbing surface and the acoustic measuring cell may be arranged with respect to one another such that gases desorbed by thermal desorption from the adsorbing surface can reach the acoustic measuring cell. When the gases reach the acoustic measuring cell, they trigger a pressure wave there that can be measured by one or more acoustic pick-up devices, such as microphones, which are arranged in the acoustic measuring cell.

A surface on which the gases to be examined are selectively adsorbed is hereby selected as a selectively adsorbing surface. This surface is exposed to a gas mixture, such as air, to test for the presence of the gases to be examined. Adsorption of the gases whose presence is to be determined is then carried out. Depending on the concentration of the gases to be examined, the selectively adsorbing surface is loaded with the gases and the acoustic measuring cell is suitably arranged. Through thermal desorption, the gases adsorbed on the selectively adsorbing surface are desorbed and arrive in the acoustic measuring cell.

Various possibilities are available for thermal desorption. The decisive factor is that the selectively adsorbing surface is heated, as is possible, for example, with an electric heating element. Compared to the structure presented in DE 199 13 220 C2 and in WO 03/026774 A1, no further excitation of the desorbed gases is necessary after desorption. It is therefore sufficient to selectively desorb the gases to be examined and to determine the concentration by measuring the pressure wave formed. This reduces equipment costs. As described below, excitation after desorption can nevertheless be useful to increase selectivity.

In an advantageous embodiment, a radiation source is available, the radiation of which can be absorbed by gases in the acoustic measuring cell, wherein the radiation source can emit radiation in a predetermined wavelength range, preferably in a wavelength range lying in the infrared range. A photoacoustic measurement is thus possible. Through the absorption of the radiation a heating of the gas occurs, which leads to gas expansion, which in turn leads to a pressure wave. This pressure wave can be measured in the acoustic measuring cell by sound-pressure pick-ups, such as, for example, microphones. The selectivity of the measurement is increased through this measure. The signal obtained depends on the absorption of the radiation by the gas. Since the radiation source can emit radiation in a predetermined wavelength range, and since different gases absorb in different wavelength ranges, a conclusion can be drawn about the type of gas from the sound-pressure signal obtained. A tunable monochromatic light source, such as, for example, a diode laser, a quantum cascade laser, or an optical parametric oscillator (OPO) is suitable as a radiation source. Likewise, a superluminescent LED can be used. Furthermore, a thermal infrared lamp with narrow-band optical filters and a unit for modulation of the infrared light are possible. Finally, a thermal infrared lamp with tunable band filter, which is characterized by a continuously adjustable transmission, can be used.

In an advantageous embodiment, a window is present in the acoustic measuring cell, through which window radiation can enter and/or a window is present through which radiation can exit. Windows are to be selected thereby which are, as far as possible, transparent for the radiation that is to pass through. Undesirable gas leakage is thus prevented through the absorption in the windows, while accepting a low photoacoustic background signal. Without windows, the photoacoustic signal could also be weakened, since only a weaker pressure wave could form, if the acoustic measuring cell had more openings. Although the acoustic measuring cell is partially open so that gas from the selectively adsorbing surface can reach the measuring cell, only a small opening is effective since the selectively adsorbing surface acts partially as a closure.

A particularly suitable gas detector is achieved if the selectively adsorbing surface is arranged on a moveable, and, in particular, rotatable, element. It is thus possible to transport the selectively adsorbing surface, without additional cost, into the area in which the adsorption of the gases is to be carried out. Subsequently, the selectively adsorbing surface on which the gases to be examined are adsorbed can be moved to the acoustic measuring cell. There, the selectively adsorbing surface, as described, can be desorbed through thermal desorption and subsequently reused for a measurement in that it is transported again into the area of the gases to be examined.

A suitable structure of the gas detector results when the moveable element is made of a transparent material that is covered with a radiation-absorbing layer on which the selectively adsorbing surface is applied. The thermal desorption can thus be carried out by radiation, which penetrates the transparent material without appreciable absorption and is then absorbed in the radiation-absorbing layer. Through absorption, a heating of the radiation-absorbing layer and thus a heating of the absorbing layer occurs, which is thermally desorbed due to the heating. With a moveable element of transparent material, a radiation source can be arranged, if desired, on the side of the moveable element facing away from the acoustic measuring cell since more space is available there.

In embodiments, a suitable shape for the moveable element is a disk. The selectively adsorbing surface can thus be easily moved by rotation of the disk into the area of the gas to be examined and to the measuring cell again. Of course, several selectively adsorbing surfaces can be mounted on the moveable element. In this way, adsorption can thus be carried out on one surface while another surface is being desorbed. Thus more measurements can be carried out at the same time. If surfaces are provided that adsorb differently, several different gases can be detected with a measuring set-up without complex changes.

One suitable possibility of supplying the heating energy necessary for thermal desorption is, as discussed above, to provide a radiation source, such as, for example, a laser. The favorable factor with heating using a laser is that heat can be supplied to the selectively adsorbing surface with comparatively high power density. The temperature necessary for desorption is thus quickly reached. The heat emitted by the selectively adsorbing surface to the surroundings is obviously lower than with a heating with low power. With low power, the heating would take longer so that a larger heat quantity would be emitted to the surroundings due to the longer duration. In particular, with a cyclical operation, that is, with a quick succession of desorption and subsequent adsorption, it is favorable if not too much heat is inserted into the selectively adsorbing surface and its immediate surroundings. After all, the surface must be sufficiently cool again for subsequent adsorption.

It is advantageous to carry out thermal desorption at different temperatures that depend on the material to be desorbed. In this manner, a conclusion can be drawn about the gas desorbed, that is the gas previously adsorbed, through the selection of the desorption temperature. For example, it is also conceivable to heat the adsorbing surface, on which the gases to be examined are adsorbed, several times in succession, with increasing temperature in each case. The signal obtained with the thermal desorption at low desorption temperature can be attributed only to gases that can already be desorbed at the lower temperature. In particular, with desorption with a laser, the quantity of energy supplied, and thus the resulting heating can be dosed as a rule without a particularly large expenditure.

It is possible to carry out a measurement when a gap is embodied between the selectively adsorbing surface and the acoustic measuring cell, which gap, of course, must not be too large. A gap of this type makes it possible to move the adsorbing surface to the acoustic measuring cell and away from it again without a disturbing contact occurring with the housing of the acoustic measuring cell. A contact of this type could be avoided only through a complex movement guidance.

The acoustic measuring cell should have an opening at least on the side facing towards the selectively adsorbing surface. In this manner the desorbed gases can reach the acoustic measuring cell easily and form a pressure wave there.

It is achieved through a suitable coordination of the size of the gap, the volume of the acoustic measuring cell and the opening thereof, that the measuring cell acoustically forms a Helmholtz resonator with a resonance frequency in the kHz range. The pressure signal is thus amplified.

The gas detector is particularly suitable for detecting contaminants in interior spaces and/or for controlling ventilation systems. With ventilation systems and/or with contaminants in interior spaces, a quick measurement is necessary, which is possible with the gas detector described. This permits a control of ventilation systems in line with needs. A control of ventilation systems in line with needs permits a high air quality with low energy consumption at the same time. Further conceivable applications of the gas detector are the detection of explosive materials and toxic gases in publicly accessible buildings. Unpleasant odors in indoor air or in the inlet air of ventilation systems can be detected. The detector is also suitable for checking that limit values are observed, such as, for example, with benzene. The gas detector is especially suitable for the detection of molecules with low vapor pressure.

The following method is particularly suitable for carrying out a measurement: First a selectively adsorbing surface is provided. This is then moved into the area in which the gas constituents are to be determined. With the above-mentioned use, this would be, for example, be indoor air. Adsorption takes place there with the gases to be examined. Subsequently, the selectively adsorbing surface is moved to an acoustic measuring cell. Through thermal desorption of the gases from the selectively adsorbing surface, which the acoustic measuring cell is suitably facing, the desorbed gases reach the acoustic measuring cell. There, the pressure wave produced by the desorbed gases is detected with one or more acoustic pick-ups, such as, for example, microphones, which are arranged in the acoustic measuring cell.

BRIEF DESCRIPTION OF THE DRAWINGS

Without loss of generality, the invention is described in more detail below based on an example. They show

DETAILED DESCRIPTION OF THE EMBODIMENTS OF THE INVENTION

The gas detector is subdivided into three units. Unit I comprises a substrate on which the selectively adsorbing areas are arranged. Unit II comprises essentially the acoustic measuring cell and the associated installations. Unit III comprises the control and the power supply of the detector.

Figure 1:
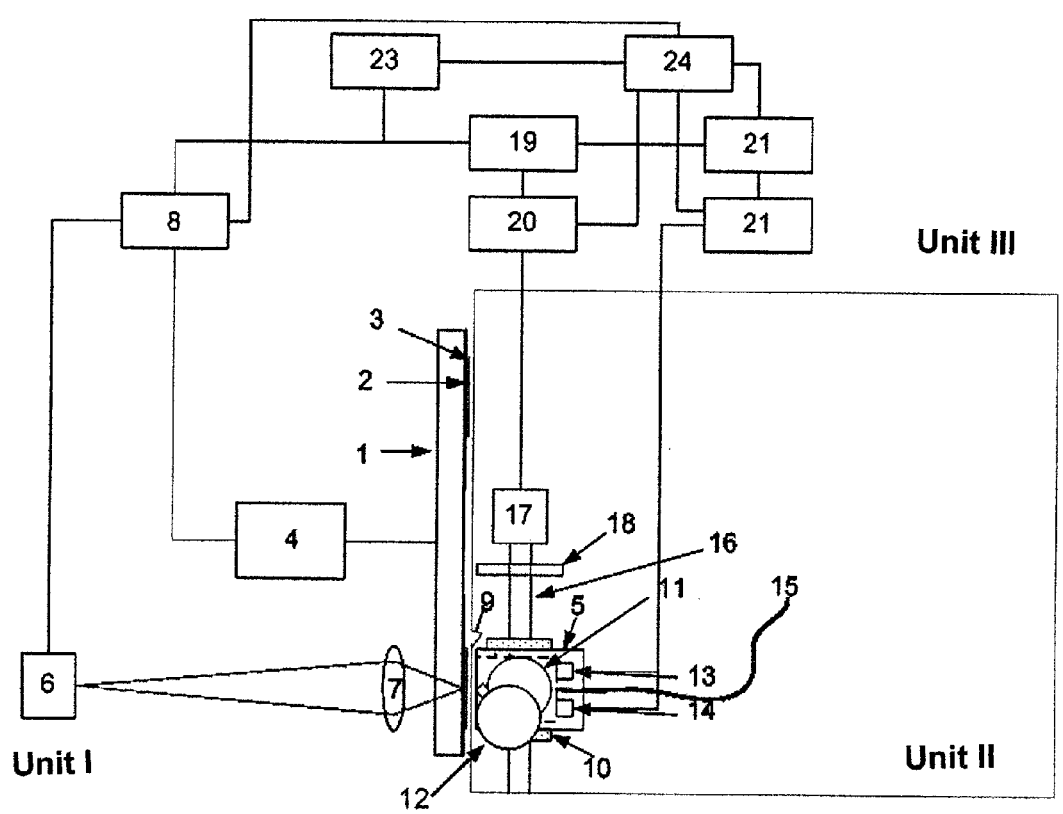
FIG. 1 illustrates an overall structure of the measuring set-up.
Figure 2:
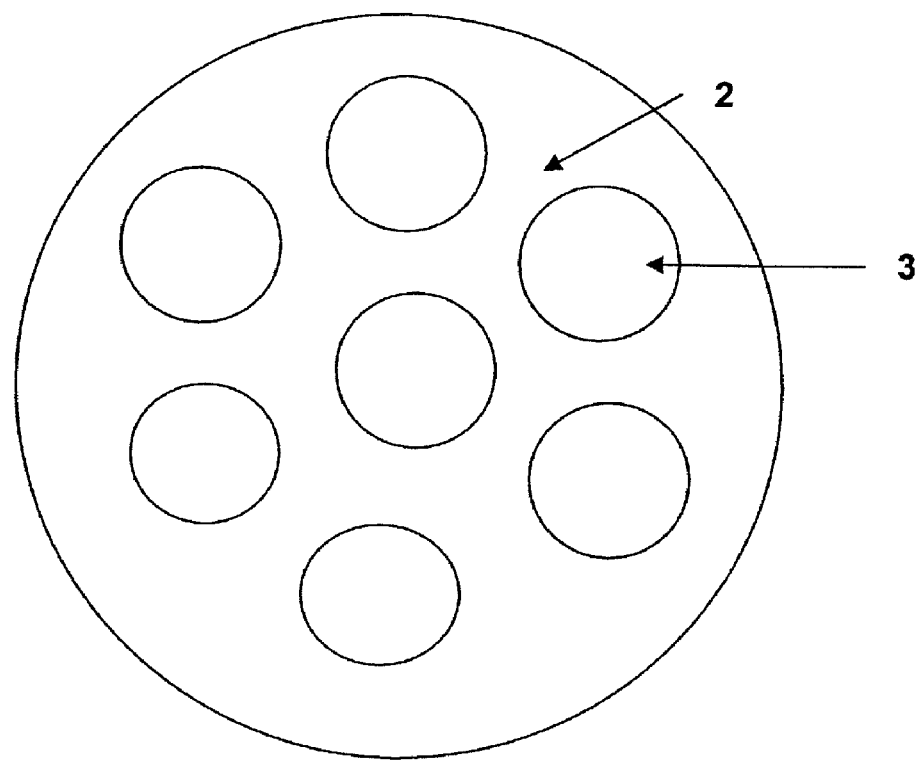
FIG. 2 illustrates a disk with several selectively adsorbing areas.

A substrate 1 transparent in the intermediate-infrared range is shown in FIG. 1. The substrate must have a low thermal conductivity and a low temperature coefficient of expansion. Glass, fused silica, and synthetic quartz are therefore suitable. A thin metal film 2, which is absorbing in the near-infrared range, is applied thereto. Areas 3, on which chemical layers are arranged for selective adsorption, are located thereon. For the selective adsorption of thiols, for example, a surface coated with silver(I) sulfide is suitable. A selectively adsorbing area is necessary for each gas to be examined, wherein several areas per component increase the selectivity of the sensor. An electric motor 4 rotates the transparent substrate 1 embodied as a disk.

FIG. 1 also shows an acoustic measuring cell 5, the interior volume of which is 1 to 2 $cm^2$. The infrared radiation of the laser 6 is concentrated in optical components, preferably a lens 7 to reach the metal film 2 through the substrate 1. Substrate 1 is transparent for the infrared radiation, while metal film 2 absorbs the infrared radiation. The metal film 2 is thus heated and emits the heat to the applied selectively adsorbing layer 3. This, in turn, leads to a thermal desorption of adsorbed gases that reach the acoustic measuring cell 5. The switching system 8 ensures that the electric motor 4 rotates the disk at the correct speed and stops it as desired at the correct time for desorption. The switching system 8 also ensures that the desorption laser 6 desorbs when the layer to be desorbed is located in front of the acoustic measuring cell 5. When needed, the switching system 8 ensures different laser current and different pulse duration of the laser 6. Thus a different heating of the metal film 2 and thus of the adsorbing area can occur, through which different components can be desorbed. The gap 9, a few tenths of a millimeter thick, guarantees an easy movement of the disk 2. The acoustic measuring cell 5 has two windows 10. These windows, which must be transparent for the radiation, permit the transmission of radiation from a radiation source 17. The acoustic measuring cell 5 further has openings 11 for the gas outlet. The openings 11 can be closed and opened by a closing mechanism 12. Microphones 13 and 14 are located opposite the continuously opened opening, which faces towards the selectively adsorbing surface. It is discernible that the connection between the selectively adsorbing surface and the acoustic measuring cell forms a first axis, the radiation 16 emitted from the radiation source 17 extends along a second axis and the gas flows out along a third axis, wherein the three axes respectively stand perpendicular to one another and form a Cartesian coordinate system.

It is also possible to illuminate the metal film 2 on the front, i.e., from the side on which the selectively adsorbing surface is located. To this end the light of the near-infrared diode laser 6 is to be guided through the acoustic measuring cell with the aid of an optical fiber 15. The radiation source 17 is preferably a very small thermal radiation source. The desired infrared wavelength range is filtered out with the aid of an interference filter 18. The desired wavelength range is the wavelength range in which the gases to be detected absorb radiation particularly well. This is usually a wavelength interval of 2 μm to 10 μm. To adjust the intensity of the infrared beam 16, the electronic system 20 adjusts the average voltage, frequency and amplitude of the modulation voltage. A modulation frequency of 20-80 Hz is usual. The photoacoustic signal generated consequently has the same modulation frequency. Furthermore, preamplifiers and filters 21 are provided for the microphones 13 and 14. They amplify the very small microphone signals to a level that is suitable for a conversion of the analog signals into digital signals. A circuit 22 is available to record the data and to evaluate them. This collects and stores the measured data, and evaluates them in order to determine the concentration of the measured components. During evaluation, the type of the selective adsorber, wavelength of the radiation 16 used, desorption temperature achieved, intensity of the acoustic signal triggered by the pressure wave caused during desorption, and intensity of the photoacoustic signal caused by the radiation 16 are taken into account. With known concentrations of gases to be examined, a calibration of the gas detector can be achieved. For further improvement, a neuronal network can be used. The parameter values, the structure and the measurement results are shown with the aid of a display circuit 23. For power supply, a power source 19 is provided. The control of the whole detector is carried out by the master controller 24.

The invention claimed is:

1. A gas detector comprising:
a selectively adsorbing surface;
an acoustic measuring cell, wherein the selectively adsorbing surface and the acoustic measuring cell are arranged with respect to one another such that gases desorbed by thermal desorption from the adsorbing surface reach the acoustic measuring cell and trigger a pressure wave; and
one or more acoustic pick-ups arranged to measure the pressure wave,
wherein the selectively adsorbing surface is arranged on a moveable element.

2. The gas detector according to claim 1 further comprising a window located in the acoustic measuring cell through which radiation at least one of enters and exits.

3. The gas detector according to claim 1, wherein the moveable element comprises a transparent material covered with a radiation-absorbing layer, and the selectively adsorbing surface is applied on the radiation absorption layer.

4. The gas detector according to claim 1, wherein the moveable element is a disk.

5. The gas detector according to claim 1 being structured and arranged to at least one of detect contaminants in interior spaces and control ventilation systems.

6. The gas detector of claim 1, wherein the one or more acoustic pick-ups are microphones.

7. The gas detector of claim 1, wherein the one or more acoustic pick-ups are arranged in the acoustic measuring cell.

8. The gas detector according to claim 1, wherein the moveable element is rotatable.

9. The gas detector of claim 1 being structured to increase in increments the thermal desorption temperature in order to selectively desorb different gases, and being arranged so that after each temperature increase, the desorbed gases reach the acoustic measuring cell.

10. The gas detector according to claim 1, further comprising at least one additional selectively adsorbing surface.

11. The gas detector according to claim 1 further comprising:
a radiation source structured and arranged to emit radiation in a predetermined wavelength range to be absorbed by gases in the acoustic measuring cell.

12. The gas detector according to claim 11, wherein the predetermined wavelength range lies in the infrared range.

13. The gas detector according to claim 1 further comprising a radiation source structured and arranged for the thermal desorption.

14. The gas detector according to claim 13 being structured to carry out the thermal desorption at different temperatures that depend on the material to be desorbed.

15. The gas detector according to claim 13, wherein the radiation source is a laser.

16. The gas detector according to claim 1 further comprising a gap formed between the selectively adsorbing surface and the acoustic measuring cell.

17. The gas detector according to claim 16, wherein the acoustic measuring cell has an opening located at least on a side facing the selectively adsorbing surface.

18. The gas detector according to claim 17, wherein the acoustic measuring cell has at least one further opening located on a side not facing the selectively adsorbing surface.

19. The gas detector according to claim 1, wherein the selectively adsorbing surface comprises a plurality of selectively adsorbing surfaces.

20. The gas detector according to claim 19, wherein the plurality of selectively adsorbing surfaces are arranged on a common substrate.

21. A gas detector comprising:
a selectively adsorbing surface;
an acoustic measuring cell, wherein the selectively adsorbing surface and the acoustic measuring cell are arranged with respect to one another such that gases desorbed by thermal desorption from the adsorbing surface reach the acoustic measuring cell and trigger a pressure wave;
one or more acoustic pick-ups arranged to measure the pressure wave; and
a gap formed between the selectively adsorbing surface and the acoustic measuring cell,
wherein the acoustic measuring cell has an opening located at least on a side facing the selectively adsorbing surface, and
wherein the gap, a volume of the acoustic measuring cell and the opening are structured and arranged to form a Helmholtz resonator.

22. A method for the analysis of gas constituents comprising:
moving a selectively adsorbing surface into an area in which the gas constituents are to be determined;
moving the selectively adsorbing surface to an acoustic measuring cell;
thermally desorbing gases from the selectively adsorbing surface, wherein the acoustic measuring cell is disposed to face the selectively adsorbing surface such that the desorbed gases reach the acoustic measuring cell; and
detecting a pressure wave produced by the desorbed gases with one or more acoustic pick-ups.

23. The method of claim 22, wherein the one or more acoustic pick-ups comprise microphones arranged in the acoustic measuring cell.

* * * * *